(12) United States Patent
Pfeiffer et al.

(10) Patent No.: US 6,325,763 B1
(45) Date of Patent: Dec. 4, 2001

(54) PORTABLE DIFFERENTIAL THERMAL BIOFEEDBACK DEVICE

(76) Inventors: Kenneth Raymond Pfeiffer, 405 Loma Media Rd., Santa Barbara, CA (US) 93103; Donald Bruce Trotter, 778 Dos Hermanos, Santa Barbara, CA (US) 93111

( * ) Notice: Subject to any disclaimer, the term of this patent is extended or adjusted under 35 U.S.C. 154(b) by 0 days.

(21) Appl. No.: 09/476,815

(22) Filed: Jan. 3, 2000

(51) Int. Cl.[7] .................................................. A61B 5/00
(52) U.S. Cl. ................................... 600/549; 128/905
(58) Field of Search ................................ 600/549, 474, 600/504, 26, 27, 28; 374/100, 112; 128/905

(56) References Cited

U.S. PATENT DOCUMENTS

| | | | |
|---|---|---|---|
| 3,942,516 | 3/1976 | Glynn et al. | 600/545 |
| 3,943,434 | * 3/1976 | Haeusler et al. | 323/366 |
| 4,246,906 | * 1/1981 | Winberg et al. | 600/549 |
| 4,306,569 | * 12/1981 | Weil et al. | 600/549 |
| 4,450,843 | 5/1984 | Barney et al. | 600/503 |
| 4,683,891 | * 8/1987 | Cornellier et al. | 600/301 |
| 4,819,656 | * 4/1989 | Spector | 600/549 |
| 5,209,494 | * 5/1993 | Spector | 273/460 |
| 5,304,112 | 4/1994 | Mrklas et al. | 600/27 |
| 5,694,939 | 12/1997 | Cowings | 600/484 |
| 5,813,766 | 9/1998 | Chen | 374/141 |
| 5,820,263 | * 10/1998 | Ciobanu | 374/111 |
| 6,056,435 | * 5/2000 | Pompei | 374/133 |

* cited by examiner

*Primary Examiner*—Eric F. Winakur
*Assistant Examiner*—Charles Marmor, II

(57) ABSTRACT

This invention is a simple, portable differential thermal biofeedback device that can be used to measure pain, anxiety, relaxation, or the defensive reflex. It compares hand temperature with head temperature and provides feedback on a voltmeter display. It can also be used to provide either hand or head temperature feedback, controlled for ambient temperature.

15 Claims, 2 Drawing Sheets

PORTABLE DIFFERENTIAL THERMAL BIOFEEDBACK DEVICE

BACKGROUND

1. Field of Invention

This invention relates to biofeedback equipment, specifically to an improved mechanism for measuring the difference in skin temperature at two different points on the body.

2. Description of Prior Art

Biofeedback generally refers to an area of psychophysiological research and applications in which a subject learns to exert conscious control over certain autonomic systems. In general, the bioelectric signal generated by a specific physiological change is amplified, and the information concerning the change is fed back to the subject in a form that allows the subject to monitor the change, and thereby learn to control the function.

Biofeedback of skin temperature is an important technique in helping people deal with various problems, including anxiety, headache, backache, and other pain. It is also used in relaxation training, which is often employed in pain management programs (Gatchel and Turk, 1996), in the treatment of phobias and ADD (attention deficit disorder, also known as ADHD or attention deficit hyperactivity disorder), and for enhancing sports performance and meditation. The typical procedure is to teach people to warm their hands by providing biofeedback of hand temperature. Hand warming indicates peripheral vasodilation (dilation of blood vessels in the hand), and is related to relaxation. Conversely, hand cooling indicates peripheral vasoconstriction (constriction of blood vessels in the hand) and indicates a reaction to pain or anxiety. Relaxation and pain thus have opposite effects on hand temperature.

Several factors confound the use of simple hand temperature as a measure of pain or relaxation, however. The first factor is ambient room temperature. For example, decreasing room temperature can lead to decreased hand temperature. More importantly, the "orienting reflex" or simple orienting to a novel stimulus causes peripheral vasoconstriction (Sokolov, 1963). The object of the present biofeedback device is to provide a better way to measure the physiological response to relaxation or pain, which is not confounded by ambient temperature or by responses such as the orienting reflex.

The physiological response to pain or other aversive stimuli is called the "defensive reflex", and includes vasodilation in the head as well as peripheral vasoconstriction. The combination of peripheral vasoconstriction and cephalic vasodilation (head warming) distinguishes the defensive reflex from the orienting reflex (Razran, 1961). Thus a more effective measure of pain or relaxation would employ thermal biofeedback of both head and hand temperature. Pain leads to an increase in head minus hand temperature, and relaxation leads to a decrease in that difference. This measure would also control for ambient room temperature, which would have about the same effect on head and hand temperature.

A previous invention, U.S. Pat. No. 3,942,516 (1976) to Glynn and James, proposed a biofeedback method and system that includes a module for measuring the difference in skin temperature between two different locations on the body. However, this invention is complex, including sampling units, amplifiers and digital processors. It also includes three other feedback modalities, EMG, EEG, and "Other", and a matrix module to integrate the information from all the feedback modalities. Because of its complexity, this invention is relatively large and expensive. The typical use is in a therapist's office, with the assistance of the therapist to set up the equipment and guide the subject. It would be difficult for an average person to purchase and use the equipment himself or herself. Moreover, the equipment could not be carried about and used whenever and wherever it is needed.

OBJECTS AND ADVANTAGES

Accordingly, several objects and advantages of our biofeedback device are:

(a) to provide a simple thermal biofeedback device;
(b) to provide an easy to use thermal biofeedback device;
(c) to provide an inexpensive thermal biofeedback device;
(d) to provide a portable thermal biofeedback device;
(e) to provide a device that measures pain;
(f) to provide a device that measures anxiety;
(g) to provide a device that measures relaxation;
(h) to provide a device that measures the defensive reflex;
(i) to provide a device that measures differential head to hand temperature;
(j) to provide a device that measures differential head to hand blood flow;
(k) to provide a differential thermal biofeedback device that controls for ambient temperature;
(l) to provide a biofeedback device for head temperature that controls for ambient temperature;
(m) to provide a biofeedback device for hand temperature that controls for ambient temperature;

Further objects and advantages of our biofeedback device will become apparent from a consideration of the drawings and ensuing description.

REFERENCE NUMERALS IN DRAWINGS

| | |
|---|---|
| 10 battery | 12 on/off switch |
| 14 resistor | 16 potentiometer |
| 18 head thermistor | 20 hand thermistor |
| 22 voltmeter | 24 enclosure base |
| 26 enclosure top | 28 circuit board |
| 30 potentiometer knob | 32 thermistor leads |

SUMMARY

This invention is a simple, portable thermal biofeedback device that can measure changes in head temperature controlled for ambient temperature, changes in hand temperature controlled for ambient temperature, and changes in differential head to hand temperature.

Figure 1:
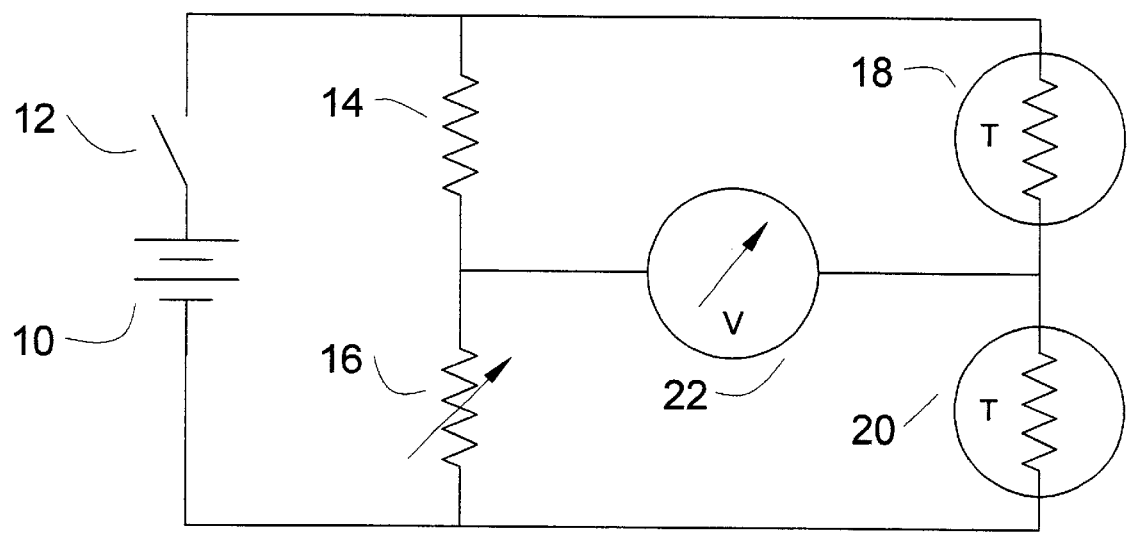
FIG. 1 is a circuit diagram of our biofeedback device.
Figure 2:
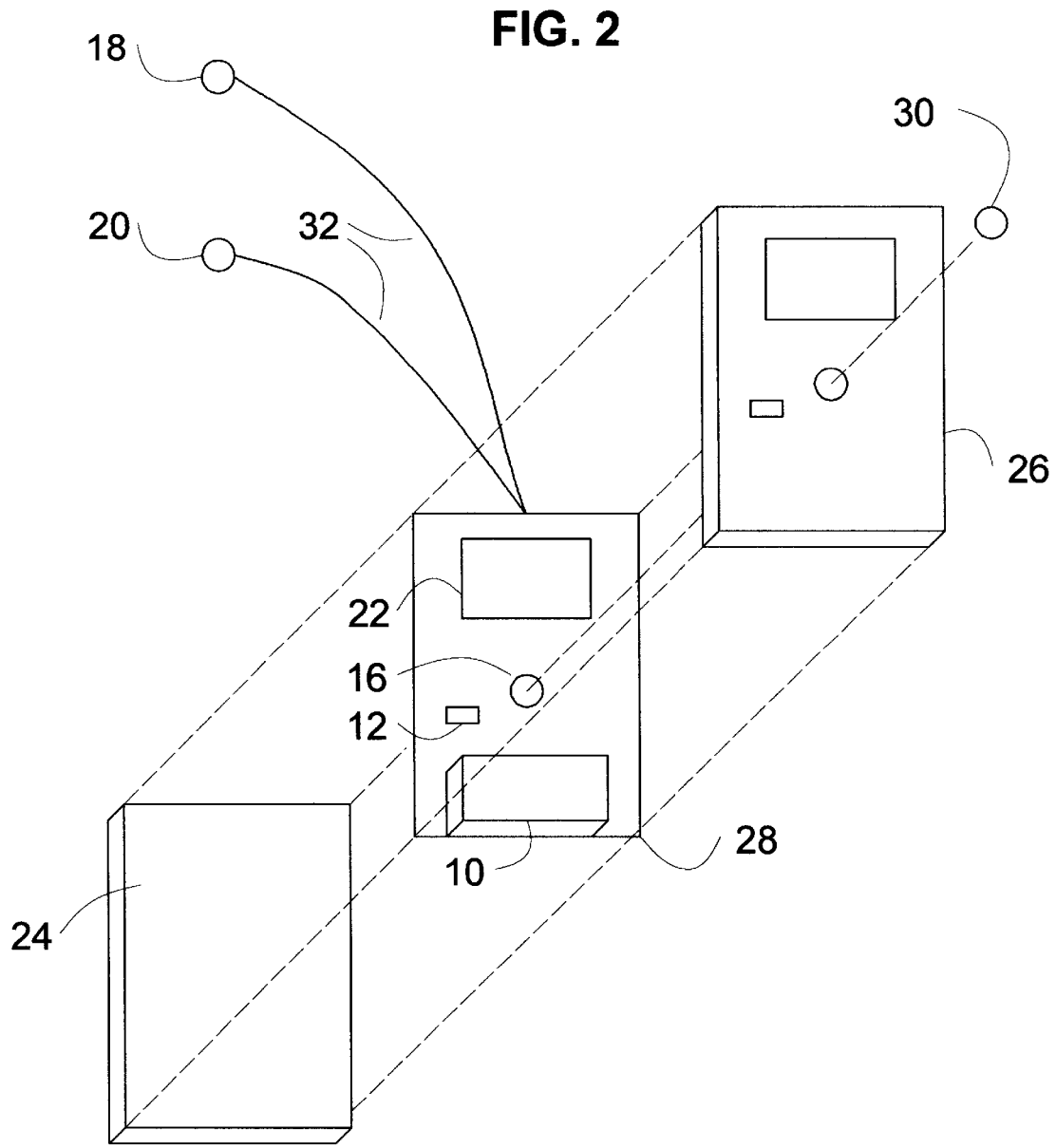
FIG. 2 is an exploded view of our biofeedback device.

DESCRIPTION OF INVENTION—FIGS. 1 to 2

A typical embodiment of the present biofeedback device is illustrated in the circuit diagram in FIG. 1. This is a resistor bridge circuit powered by a 9-volt battery 10 and controlled by on/off switch 12. The bridge is comprised of 10K Ω thermistors 18 and 20, along with 10K Ω resistor 14 and 10K Ω linear potentiometer 16. Voltmeter 22, composed of an LCD single chip A/D converter and an LCD display, responds to changes in resistance of the thermistors, one of which is attached to the head and one to the hand. The potentiometer can be used to adjust the initial voltmeter readout to a desired number. Although specific values have been assigned to the above electronic components such as resistors and thermistors, these components could have other values, and the voltmeter and battery could also be of other types.

FIG. 2 is an exploded view of a typical embodiment of the biofeedback device. A printed circuit board 28 is enclosed between the bottom 24 and top 26 of the lightweight plastic case. On the circuit board are mounted the battery 20, the on/off switch 12, the potentiometer 16, and the voltmeter 22. The knob 30 controls the potentiometer. The head thermistor 18 and the hand thermistor 20 are connected to the printed circuit board with flexible wire leads 32. The thermistors are connected to the head or hand of the subject with adhesive, elastic bands, velcro, or some other material.

OPERATION OF INVENTION—FIGS. 1 to 2

The subject attaches the head thermistor 18 to the center of the forehead, and the hand thermistor 20 to the center of the pad of the index finger of either hand. The subject turns on the device with switch 12 and then adjusts the voltmeter, including a display, 22 to a predetermined value by using potentiometer 16. Subsequent changes in voltmeter readings reflect changes in head versus hand temperature, and provide feedback to the subject.

One alternate mode of operation is to connect the hand thermistor to the hand but leave the head thermistor unconnected to the body. This mode will provide hand temperature feedback to the subject, controlled for ambient temperature. Another alternate mode of operation is to connect the head thermistor to the head, but leave the hand thermistor unconnected to the body. This mode will provide head temperature feedback to the subject, controlled for ambient temperature.

Conclusion, Ramifications, and Scope of Invention

Thus the reader can see that the invention provides a simple, inexpensive, easy to use, portable differential thermal biofeedback device.

While the above description contains many specificities, these should not be construed as limitations on the scope of the invention, but rather as an exemplification of one preferred embodiment. Many other variations are possible. For example, the device could be further miniaturized and worn in the style of a pager or wristwatch. The case could be made of a different material, or a different type of battery and voltmeter display could be used. Instead of a voltmeter display, auditory feedback could be given with a tone generator. The thermistors could also be placed at points on the body other than the head and hand to provide thermal biofeedback of those points.

Accordingly, the scope of the invention should be determined not by the embodiment illustrated, but by the appended claims and their legal equivalents.

We claim:

1. A biofeedback device for measuring relaxation, pain, anxiety, and the defensive reflex independent of the orienting reflex, and changes in ambient temperature, comprising a display for providing visual feedback to the user and means for measuring differences between head and hand temperatures which differences are inputted to said display.

2. The biofeedback device of claim 1 wherein said display is an LCD display.

3. The biofeedback device of claim 1 wherein said means for measuring differences between head and hand temperature comprises a thermistor adapted to be attached to the head of a subject, a thermistor adapted to be attached to the hand of a subject, and means for measuring the difference in resistance of said thermistors.

4. The biofeedback device of claim 3 wherein said means for measuring the difference in resistance of said thermistors comprises a voltmeter and a resistor bridge including said thermistors.

5. The biofeedback device of claim 1 wherein a readout of said display is adjusted with a potentiometer.

6. The biofeedback device of claim 1 wherein said device is turned on and off with a switch.

7. The biofeedback device of claim 1 wherein said device is battery powered.

8. The biofeedback device of claim 1 wherein said display and said means for measuring differences between head and hand temperature are contained in an enclosure that is not substantially larger than an average size adult human hand, whereby a user can conveniently carry the device in one hand.

9. A method for measuring relaxation, pain, anxiety, and the defensive reflex independent of the orienting reflex and changes in ambient temperatures; the method comprising:

providing a biofeedback device, including a display, a first thermistor, a second thermistor, a resistor bridge, and a voltmeter;

attaching the first thermistor to the head of a subject;

attaching the second thermistor to the hand of a subject;

measuring a difference in resistance of said first thermistor and said second thermistor, using the resister bridge and voltmeter; and providing feedback on said display.

10. The method of claim 9 whereby a user can treat anxiety.

11. The method of claim 9 whereby a user can treat phobias.

12. The method of claim 9 whereby a user can treat pain.

13. The method of claim 9 whereby a user can treat ADD and ADHD.

14. The method of claim 9 whereby a user can enhance sports performance.

15. The method of claim 9 whereby a user can enhance meditation.

* * * * *